United States Patent
Farnworth

(10) Patent No.: US 7,159,752 B2
(45) Date of Patent: *Jan. 9, 2007

(54) CONTINUOUS MODE SOLDER JET APPARATUS

(75) Inventor: Warren M. Farnworth, Nampa, ID (US)

(73) Assignee: Micron Technology, Inc., Boise, ID (US)

(*) Notice: Subject to any disclaimer, the term of this patent is extended or adjusted under 35 U.S.C. 154(b) by 186 days.

This patent is subject to a terminal disclaimer.

(21) Appl. No.: 10/616,184

(22) Filed: Jul. 7, 2003

(65) Prior Publication Data

US 2004/0026479 A1 Feb. 12, 2004

Related U.S. Application Data

(63) Continuation of application No. 10/159,000, filed on May 30, 2002, now Pat. No. 6,588,645, which is a continuation of application No. 09/924,525, filed on Aug. 8, 2001, now Pat. No. 6,443,350, which is a continuation of application No. 09/569,215, filed on May 11, 2000, now Pat. No. 6,325,271, which is a continuation of application No. 09/388,032, filed on Sep. 1, 1999, now Pat. No. 6,082,605, which is a continuation of application No. 08/989,578, filed on Dec. 12, 1997, now Pat. No. 5,988,480.

(51) Int. Cl.
*B23K 31/02* (2006.01)
*B23K 35/12* (2006.01)

(52) U.S. Cl. .................. 228/33; 228/260; 228/262; 239/102.2; 347/76; 347/77

(58) Field of Classification Search ............ 228/33, 228/260, 262; 347/68, 76, 77, 75; 239/102.2, 239/85; 222/591
See application file for complete search history.

(56) References Cited

U.S. PATENT DOCUMENTS

| | | |
|---|---|---|
| 3,641,588 A | 2/1972 | Metz |
| 4,650,694 A | 3/1987 | Dressler et al. |
| 4,817,851 A | 4/1989 | Kolesar et al. |
| 4,872,905 A | 10/1989 | Bourne et al. |
| 4,981,249 A | 1/1991 | Kawashima et al. |
| 5,226,948 A | 7/1993 | Orme et al. |
| 5,229,016 A | 7/1993 | Hayes et al. |
| 5,259,593 A | 11/1993 | Orme et al. |
| 5,266,098 A | 11/1993 | Chun et al. |
| 5,364,011 A | 11/1994 | Baker et al. |
| 5,377,961 A | 1/1995 | Smith et al. |
| 5,379,931 A | 1/1995 | Van Schaik |
| 5,411,602 A | 5/1995 | Hayes |
| 5,455,606 A | 10/1995 | Keeling et al. |

(Continued)

FOREIGN PATENT DOCUMENTS

SU 1682039 10/1991

*Primary Examiner*—Jonathan Johnson
(74) *Attorney, Agent, or Firm*—TraskBritt

(57) ABSTRACT

A solder jet apparatus is disclosed. The solder jet apparatus is a continuous mode solder jet that includes a blanking system and raster scan system. The use of the raster scan and blanking systems allows for a continuous stream of solder to be placed anywhere on the surface in any desired X-Y plane. This allows for greater accuracy as well as greater product throughput. Additionally, with the raster scan system, repairs to existing soldered surfaces can be quickly and easily performed using a map of the defects for directing the solder to the defects.

9 Claims, 2 Drawing Sheets

U.S. PATENT DOCUMENTS

| | | |
|---|---|---|
| 5,481,288 A | 1/1996 | Keeling et al. |
| 5,520,715 A | 5/1996 | Oeftering |
| 5,545,465 A | 8/1996 | Gaynes et al. |
| 5,560,543 A | 10/1996 | Smith et al. |
| 5,585,629 A | 12/1996 | Doran et al. |
| 5,597,110 A | 1/1997 | Melton et al. |
| 5,643,353 A | 7/1997 | Wallace et al. |
| 5,736,074 A | 4/1998 | Hayes et al. |
| 5,746,844 A | 5/1998 | Sterett et al. |
| 5,747,102 A | 5/1998 | Smith et al. |
| 5,772,106 A | 6/1998 | Ayers et al. |
| 5,779,971 A | 7/1998 | Tsung Pan et al. |
| 5,810,988 A | 9/1998 | Smith, Jr. et al. |
| 5,855,323 A | 1/1999 | Yost et al. |
| 5,868,305 A | 2/1999 | Watts, Jr. et al. |
| 5,891,212 A | 4/1999 | Tang et al. |
| 5,894,980 A | 4/1999 | Orme-Marmarelis et al. |
| 5,894,985 A | 4/1999 | Orme-Marmarelis et al. |
| 5,938,102 A | 8/1999 | Muntz et al. |
| 5,988,480 A | 11/1999 | Farnworth |
| 6,036,777 A | 3/2000 | Sachs |
| 6,070,973 A | 6/2000 | Sachs et al. |
| 6,082,605 A | 7/2000 | Farnworth |
| 6,186,192 B1 | 2/2001 | Orme-Marmarelis et al. |
| 6,202,734 B1 | 3/2001 | Sackinger et al. |
| 6,213,356 B1 | 4/2001 | Nakasu et al. |
| 6,224,180 B1 | 5/2001 | Pham-Van-Diep et al. |
| 6,264,090 B1 | 7/2001 | Muntz et al. |
| 6,276,589 B1 | 8/2001 | Watts, Jr. et al. |
| 6,325,271 B1 | 12/2001 | Farnworth |
| 6,350,494 B1 | 2/2002 | Farnworth |
| 6,443,350 B1 | 9/2002 | Farnworth |
| 2001/0048017 A1* | 12/2001 | Farnworth .................. 228/33 |
| 2002/0031612 A1 | 3/2002 | Farnworth |
| 2002/0145030 A1* | 10/2002 | Farnworth .................. 228/33 |
| 2004/0026479 A1* | 2/2004 | Farnworth .................. 228/33 |

\* cited by examiner

CONTINUOUS MODE SOLDER JET APPARATUS

CROSS-REFERENCE TO RELATED APPLICATIONS

This application is a continuation of application Ser. No. 10/159,000, filed May 30, 2002, now U.S. Pat. No. 6,588,645, issued Jul. 8, 2003, which is a continuation of application Ser. No. 09/924,525, filed Aug. 8, 2001, now U.S. Pat. No. 6,443,350, issued Sep. 3, 2002, which is a continuation of application Ser. No. 09/569,215, filed May 11, 2000, now U.S. Pat. No. 6,325,271, issued Dec. 4, 2001, which is a continuation of application Ser. No. 09/388,032, filed Sep. 1, 1999, now U.S. Pat. No. 6,082,605, issued Jul. 4, 2000, which is a continuation of application Ser. No. 08/989,578, filed Dec. 12, 1997, now U.S. Pat. No. 5,988,480, issued Nov. 23, 1999.

BACKGROUND OF THE INVENTION

The present invention relates generally to applying solder to a substrate and, more particularly, to the selected placement of solder using a solder jet.

Depositing solder selectively on a substrate is well known. Different techniques include stenciling or screening a solder paste onto the substrate, using solder balls selectively placed where metal contact is desired, and chemically vapor depositing the metal onto the surface of the substrate. Each one of these methods has advantages and disadvantages.

The use of a stencil to fabricate a conductive trace pattern on the surface allows for precise alignment and placement of the solder. Unfortunately, the stencils are expensive to design and produce and they wear out after repeated use. When they wear out, solder seeps through the worn stencil areas across those areas where no solder is desired, causing shorts, or no solder is being placed where it is needed, causing a breach or open connection. These areas have to be repaired and if these types of conditions are repeated with any type of frequency, the stencil must be replaced with a new stencil. Additionally, stencils require periodic cleaning, which adds another processing step to clean the stencil as well as lessens the useful life of the stencil.

The use of solder balls has been a tremendous advance in the art of electrically connecting a device to the surface of a printed circuit board. Solder balls, however, have quality control problems as their critical dimensions continue to decrease. The ability to produce balls of the same diameter consistently decreases as the diameter decreases. Thus, for some diameters of solder balls, the range of acceptable product can be solder balls having diameters more than twice the desired diameter. Or, they can have diameters half the size of the desired diameter. This requires that the tolerances at the surface contact level of a substrate, such as a semiconductor device, must allow for a solder ball having a diameter that is from 50% smaller to 100% larger than the specified size. Further, working with solder balls is difficult because of their size and the methods needed to place them accurately. When they fail to be placed accurately, or are missing entirely, problems occur in the resulting assembly of a semiconductor device attached to a substrate that must be corrected. These problems include shorts or opens that must be fixed. No easy solution yet exists for repairing missing or improperly sized solder balls after a semiconductor device has been mechanically attached in place on a substrate.

Chemical vapor deposition (CVD) allows for precise alignment of conductive traces and for batch processing. CVD does have limitations however. These limitations include being unable to place the package directly on the surface of the printed circuit board (PCB) immediately after depositing the metal on the surface since a cooling step is typically needed. Further, clean conditions are always necessary when using CVD, which requires expensive equipment and control. Additionally, when clean conditions do not exist, shorts or opens in assemblies can occur that need to be repaired once they are discovered.

A new approach to deposit solder on a surface, such as a printed circuit board (PCB), is to deposit the solder using a solder jet, similar to the manner in which ink jets deposit ink onto paper for printing. The ink jet technology is well established, but due to different problems associated with solder, ink jet technology is not directly applicable to solder jet technology. For example, solder jets use molten melt as a print agent, whereas ink jets use heated water-based ink. Since the print agent is metal in solder jets, the viscosities and densities are much different as are the operating temperatures. Thus, applying ink jet solutions to solder jet problems is impractical.

One typical solder jet apparatus has recently been developed by MPM Corporation. The solder jet apparatus takes liquid solder and forms it into a stream of droplets that have a uniform size and composition. The formation of the droplets involves generating a consistent pressure coupled with a vibration force sufficient enough to dislodge the drops from the jet nozzle in a steady state with a uniform size and consistency. Once the solder droplets are formed, gravity forces them downward where they impact on the surface of the substrate. The solder droplets pass through a charging electrode to impart a charge on the metal droplets.

The system operates using a binary control that either allows the droplets to impact on the surface or to be removed into a droplet catcher for recycling when no droplets are desired. Since the droplets were charged at one point, an electric field or pulse can be asserted, causing the droplets to either continue to the surface or to fall into the catcher. With this system, the exact position of the droplets is known and never varies. Thus, the substrate must be moved to the desired grid for the droplets to impact the area desired to be soldered. This results in a highly inefficient system since the substrate must be stopped for each application of solder to a new location. This also involves greater mechanical complexity since the table holding the substrate, or the solder jet apparatus itself, must be moved and aligned properly before solder can be deposited.

Accordingly, what is needed is a solder applicator that allows for greater precision in placing the droplets along with increased efficiency in product throughput.

SUMMARY OF THE INVENTION

According to the present invention, a solder jet apparatus is disclosed. The solder jet apparatus is a continuous mode solder jet that includes a blanking system and raster scan system. The use of the raster scan and blanking systems allows for a continuous stream of solder to be placed anywhere on the surface in any desired X-Y plane. This allows for greater accuracy as well as greater product throughput. Additionally, with the raster scan system, repairs to existing soldered surfaces can be quickly and easily performed using a map of the defects for directing the solder to the defects.

DETAILED DESCRIPTION OF THE INVENTION

Figure 1:
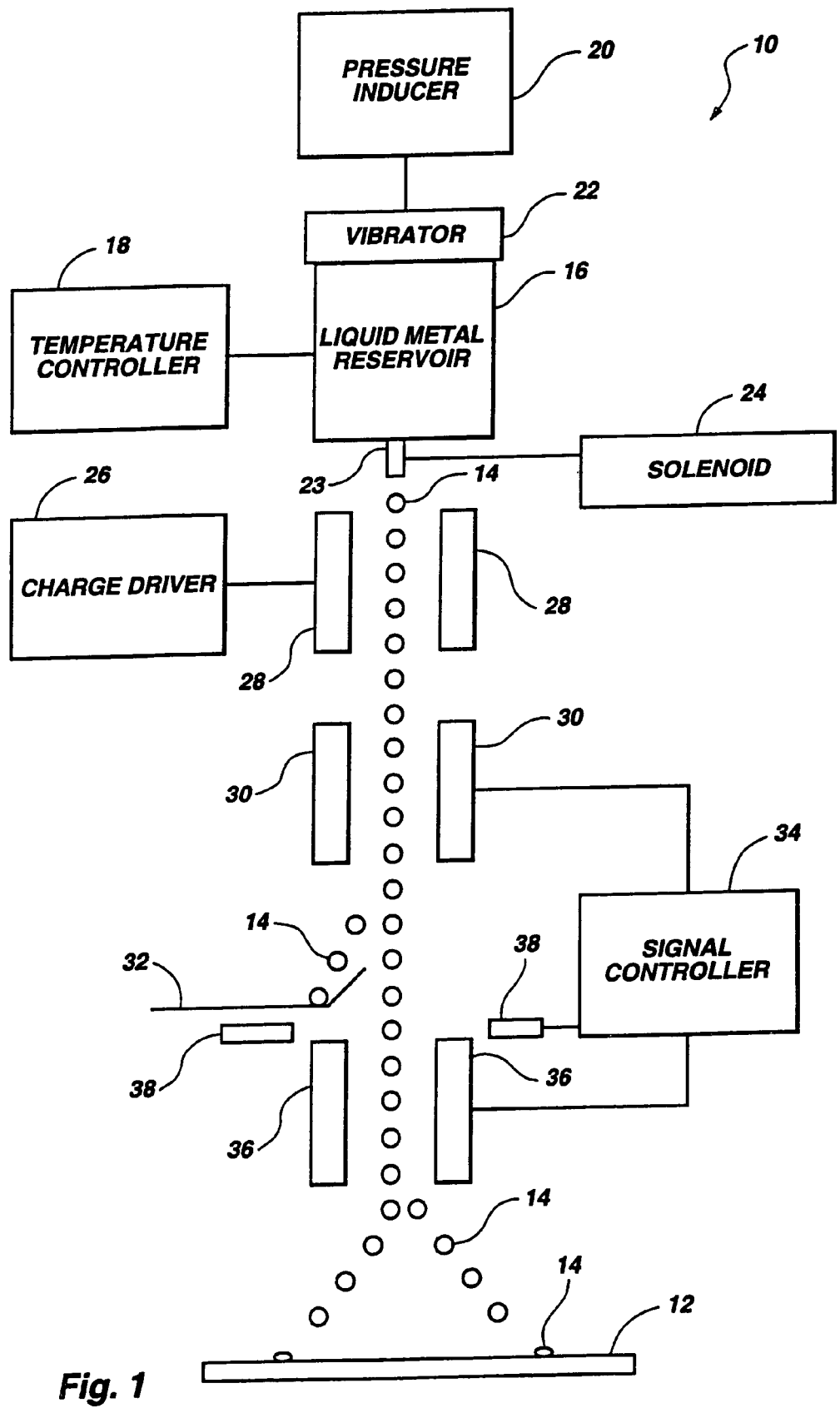
FIG. 1 is a schematic block diagram of a solder jet apparatus according to the present invention.

A solder jet apparatus 10 is depicted in the schematic block diagram of FIG. 1. Solder jet apparatus 10 deposits metal on substrate 12 in the form of solder droplets 14. The solder droplets 14 can be directed in an X-Y plane of deflection using a raster scan and blanking system. This allows the solder droplets to be "written" on substrate 12.

The solder droplets 14 are formed from melted metal held in liquid metal reservoir 16. A temperature controller 18 is connected to liquid metal reservoir 16 so that the temperature of the liquid metal held in the reservoir can be kept at a desired temperature that leads to optimum droplet formation and release. For example, the solder eutectic temperature at the point of release is 190° C. and its temperature at impact is 183° C. To prevent solder droplets 14 from cooling too rapidly or from oxidizing, a constant surrounding temperature is provided and, if desired, the apparatus can be placed in a container that is either under vacuum or is filled with an inert gas.

The solder droplets 14 can be formed by the application of a driving pressure and a sufficient vibration force. The driving pressure can be provided by pressure inducer 20, which is comprised of a piezoelectric crystal that is driven by a tuning frequency sufficient enough to cause pressure to build up in liquid metal reservoir 16. The mechanical vibration is generated by vibrator 22, which comprises a second piezoelectric crystal that is driven by another tuning frequency, causing liquid metal reservoir 16 to vibrate. The timing of the pressure and the vibrations is established so as to produce uniform droplets of the same consistency. Once the solder droplets 14 are formed, the vibration releases them from liquid metal reservoir 16 and the force of gravity draws them down at a predictable velocity.

Liquid metal reservoir 16 further includes a solder jet nozzle 23, which is opened and closed via a solenoid 24. The aperture of solder jet nozzle 23 is selected with a size sufficient enough to generate the droplets of a desired size. The solder droplets 14 are formed having a diameter of micron size, ranging from 40–300. When solenoid 24 is activated, it either closes or opens solder jet nozzle 23.

Solder droplets 14 pass through several zones before either being deposited on substrate 12 or recycled back to liquid metal reservoir 16. The first zone is a charging field driven by charge driver 26. Charge driver 26 causes charge electrodes 28 to generate an electric field therebetween. As solder droplets 14 pass past charge electrodes 28, they are imparted with an electric charge. With this charge, solder droplets 14 can be deflected at later stages as appropriate.

The second zone is a blanking zone that uses blanking electrodes or coil 30. The blanking electrodes are activated having sufficient electric field so as to cause solder droplets 14 to deflect to a catcher 32. This is the return function of the scanning function as is described below. Catcher 32 catches the liquid solder and causes the metal to be recycled to liquid metal reservoir 16. This prevents solder droplets 14 from depositing on the surface of substrate 12. This blanking can be done in a selective manner so that droplets are deposited in some locations, but not others. Blanking electrodes or coil 30 are controlled by signal controller 34. Signal controller 34 can be a signal processor such as a computer system. The computer system allows greater control of solder droplets 14 by programming the blanking electrodes or coil 30 to turn on and off in a desired sequence so as to pattern the substrate with a desired solder pattern. An alternative embodiment can include an air jet system if the electrical pulse is insufficient to remove the droplets. A photo cell can be located above the air jet system in order to ensure proper timing of electrical pulses or the air pressure.

The third zone is the raster scan system and includes electrostatic deflection plates or magnetic coil 36. Electrostatic deflection plates 36 are charged by signal controller 34 so that solder droplets 14 are deflected in either the horizontal X-direction or the vertical Y-direction, or both. Further, the solder droplets 14 can be held in a steady position in the X-Y plane in order to build up the solder to a desired height. Since the droplet stream now scans in the X- and Y-directions, the substrate 12 can now stay stationary throughout the droplet application process. Signal controller 34 can be programmed to perform a variety of soldering patterns for placing solder droplets 14 on substrate 12. For example, a CAD/CAM system programmed with a desired output sends signals to blanking electrodes 30 and to electrostatic deflection plates 36 to guide the droplet stream in the desired pattern of placing droplets in certain locations, but not in others. Additionally, when the "stream" of solder droplets 14 is returned to the beginning of the horizontal scan, blanking electrodes 30 cause the solder droplets 14 to deflect to catcher 32 so as not to "write" across the substrate during the return scan. The location of blanking electrodes 30 and electrostatic deflection plates 36 can be switched, if desired.

An electronic light sensor 38, which connects to signal controller 34, is positioned so that the solder droplets 14 pass through the electronic light sensor 38. Electronic light sensor 38 is used to count the number of solder droplets 14 passing by. This allows signal controller 34 to monitor the droplet output and either blank or pass droplets as needed.

Figure 2:
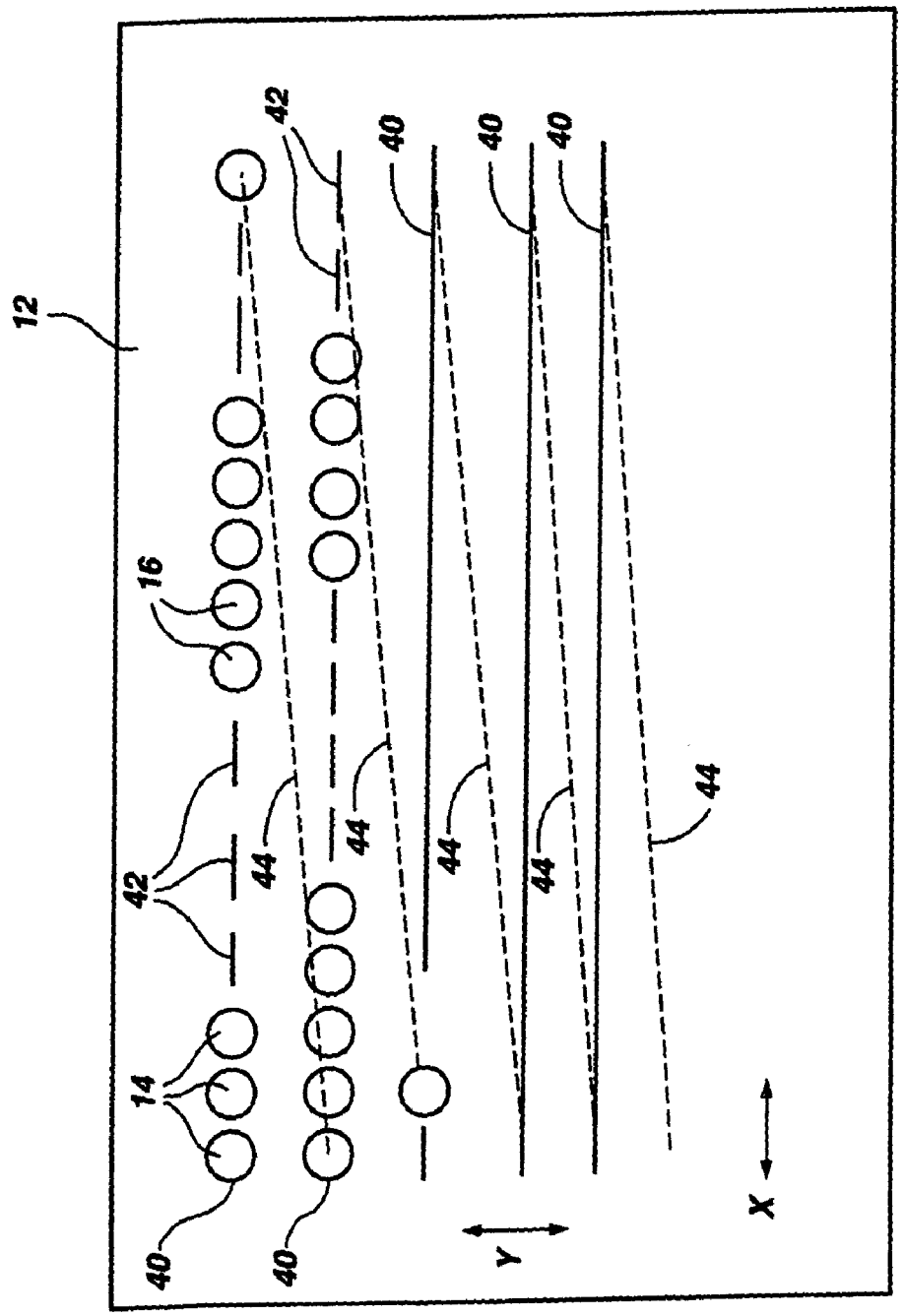
FIG. 2 is a top plan view of a substrate having solder deposited according to the solder jet apparatus of FIG. 1.

FIG. 2 is a top plan view of the surface of substrate 12 as solder droplets 14 are deposited. A first line 40 scans across the surface, depositing solder droplets 14 in selected positions and leaving blanks 42 in the remaining positions. A return scan line 44, which is ghosted, indicates when the stream of droplets is caught by catcher 32 as the stream returns to the beginning of the next line 40. This process is repeated as often as is necessary with catcher 32 collecting all the blank spots and scan returns. Alternatively, solenoid 24 can be activated to close solder jet nozzle 23 during the return scan. This also prevents unwanted solder droplets 14 from depositing on the surface of substrate 12.

The type of solder used with the solder jet apparatus 10 can include any type of metal solder such as, for example, 63/37 PbSN, 62/36/2PbSnAa, In/Sn.

The solder jet apparatus 10 can be used for many types of solder application. One type of application includes that of applying uniform solder balls, in the form of solder droplets, to the substrate 12. This provides a universal ball applicator system. Further, the system can repair particular locations where the solder ball application process has failed to insert a desired solder ball. In order to repair any and all solder ball defects, a scan of the surface of substrate 12 can be provided and then a map of the defective areas can be programmed to the signal controller 34. This allows for a rapid repair of the surface of substrate 12 where solder balls had been omitted. Another application is to pre-tin a location on substrate 12. Pre-tinning is accomplished by applying one or more droplets to the same location or to apply droplets in such a manner as to thoroughly cover the surface of substrate 12 or a grid section of substrate 12.

Similar to pre-tinning is pre-plating a board. Pre-plating a board involves applying solder droplets over the entire surface area of the board to cover it with a metal plate. An exposed portion of the board can be selected where desirable. Typically, this area is along the edge of the board either on one edge, two edges, or all four edges, or can be in the center section of the board. Prior methods of pre-plating a board resulted in a problem known as "measling." Measling is where small holes exist in the plating surface that lead to electrical defaults. The use of the solder jet apparatus 10 allows the system to eliminate the measling locations by applying solder directly to those openings. Additionally, using the pre-plating process provided by solder jet apparatus 10 eliminates measling entirely. Just as pre-plated boards may have measling problems, boards that had been stenciled with solder paste had similar problems. These problems can include openings or gaps in the stenciled design. Again, a map of the surface defects can be ascertained and then used by the signal controller 34 to make appropriate correction and repair to those particular problem points. Additionally, large areas can be printed using the X-Y motion of the table in combination with the X-Y slowing of the solder application. Also, the final ball size can be changed on demand. Further, in prior ball application systems that apply 7 balls/sec, the board needs to be moved to a new location. With this invention, no relocation time is required, thus reducing processing time.

While the present invention has been described in terms of certain preferred embodiments, it is not so limited, and those of ordinary skill in the art will readily recognize and appreciate that many additions, deletions and modifications to the embodiments described herein may be made without departing from the scope of the invention as hereinafter claimed.

What is claimed is:

1. A liquid solder jet apparatus for depositing a stream of liquid solder droplets on selected bond pads of at least one semiconductor die of a substrate having a surface having a plurality of locations of contact pads thereon extending throughout the surface, each location of the plurality of locations on the surface having a start point and an endpoint, comprising:

a continuous stream generator for producing a stream of liquid metal solder droplets, the liquid metal solder droplets having a uniform size within a consistent predetermined range, the consistent predetermined range of uniform size metal solder droplets being within a size of the selected bond pads of the at least one semiconductor die and the contact pads of the substrate;

a stream director for selectively directing the stream of liquid metal solder droplets after being produced by the continuous stream generator onto the selected bond pads of the at least one semiconductor die of the substrate, the stream director comprising a raster scanner scanning the stream of liquid metal solder droplets, the raster scanner including:

an electrical charge generator for charging at least a portion of the liquid metal solder droplets of the stream of liquid metal solder droplets with an electrical charge;

a stream blanking device for intermittently blanking at least some of the liquid metal solder droplets of the stream of liquid metal solder droplets; and an electrically charged droplet deflector for deflecting at least one electrically charged liquid metal solder droplet of the stream of liquid metal solder droplets in a first direction and a second direction for deposition at a location of the plurality of locations extending throughout the surface of the substrate when the substrate remains stationary;

a reservoir for holding liquid metal solder;

a vibrator for causing formation of the stream of liquid metal solder droplets; and a temperature controller connected to the reservoir for maintaining the liquid metal solder in a liquid state.

2. The apparatus according to claim 1, wherein the continuous stream generator comprises:

a pressure inducer; and the vibrator comprises a vibrator connected to the pressure inducer for causing formation of the stream of liquid metal solder droplets in connection with the pressure inducer.

3. The apparatus according to claim 2, wherein the pressure inducer comprises a piezoelectric crystal operating at a desired frequency.

4. The apparatus according to claim 2, wherein the vibrator comprises a piezoelectric crystal operating at a selected frequency to form liquid metal droplets having a size in a range of micron size droplets of a liquid metal solder.

5. The apparatus according to claim 1, wherein the continuous stream generator includes a solder jet nozzle having an aperture producing a consistent range of droplets of the liquid metal solder for forming the stream of liquid metal solder droplets.

6. The apparatus according to claim 5, wherein the continuous stream generator further includes a solenoid connected to the solder jet nozzle.

7. The apparatus according to claim 1, wherein the stream blanking device at least provides blanking of the at least some of the stream of liquid metal solder droplets when the stream of liquid metal solder droplets is positioned between the endpoint of a first location of the plurality of locations extending throughout the surface of the substrate and the start point of a second location of the plurality of locations extending throughout the surface of the substrate.

8. The apparatus according to claim 1, wherein the stream blanking device comprises:

a deflector field device selectively deflecting at least one droplet of the stream of liquid metal solder droplets; and a droplet catcher catching the at least one droplet which has been deflected from the stream of liquid metal solder droplets prior to the at least one droplet which has been deflected from the stream of liquid solder droplets being deposited on at least one bond pad of the at least one semiconductor die of the substrate.

9. The apparatus according to claim 1, wherein the stream director includes a programmable direction controller for determining a direction of the stream of liquid metal solder droplets.

* * * * *

UNITED STATES PATENT AND TRADEMARK OFFICE
CERTIFICATE OF CORRECTION

PATENT NO. : 7,159,752 B2
APPLICATION NO. : 10/616184
DATED : January 9, 2007
INVENTOR(S) : Warren M. Farnworth It is certified that error appears in the above-identified patent and that said Letters Patent is hereby corrected as shown below:

In the drawings:
        In FIG. 2,       change reference numeral "16" to --14--

In the specification:
        COLUMN 4, LINE 54,   change "62/36/2PbSnAa," to --62/36/2PbSnAg,--

Signed and Sealed this

Eighth Day of January, 2008

JON W. DUDAS
*Director of the United States Patent and Trademark Office*

UNITED STATES PATENT AND TRADEMARK OFFICE
CERTIFICATE OF CORRECTION

PATENT NO. : 7,159,752 B2
APPLICATION NO. : 10/616184
DATED : January 9, 2007
INVENTOR(S) : Warren M. Farnworth It is certified that error appears in the above-identified patent and that said Letters Patent is hereby corrected as shown below:

Replace FIG. 2 with the following amended figure:

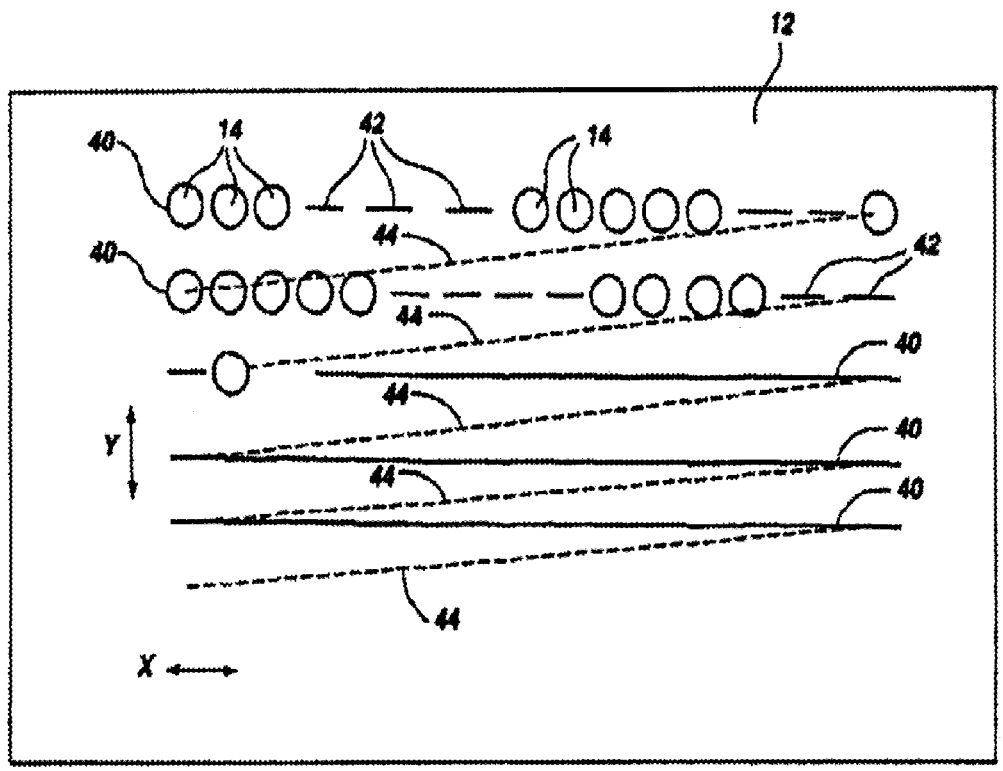

Fig. 2